United States Patent [19]

Kedem

[11] Patent Number: 5,133,359
[45] Date of Patent: Jul. 28, 1992

[54] HARD TISSUE BIOPSY INSTRUMENT WITH ROTARY DRIVE

[75] Inventor: Dan Kedem, Rehovot, Israel

[73] Assignee: Du-Kedem Technologies Ltd., Rehovot, Israel

[21] Appl. No.: 652,740

[22] Filed: Feb. 8, 1991

[30] Foreign Application Priority Data

Nov. 14, 1990 [IL] Israel ............................. 96352

[51] Int. Cl.⁵ .................................. A61B 10/00
[52] U.S. Cl. ............................... 128/754; 128/755; 606/172; 606/180
[58] Field of Search ............... 128/754, 755, 751, 753; 604/117, 156, 158, 159, 161, 272; 606/167, 172, 180, 181, 184, 185, 171

[56] References Cited

U.S. PATENT DOCUMENTS

| | | | |
|---|---|---|---|
| 2,919,692 | 1/1960 | Ackermann | 128/754 |
| 4,306,570 | 12/1981 | Matthews | 128/754 |
| 4,461,305 | 7/1984 | Cibley | 128/754 |
| 4,696,308 | 9/1987 | Meller et al. | 128/754 |
| 4,710,171 | 12/1987 | Rosenberg | 604/117 |
| 4,717,383 | 1/1988 | Phillips et al. | 604/135 |
| 4,756,708 | 7/1988 | Martin | 604/93 |
| 4,790,329 | 12/1988 | Simon | 128/749 |
| 4,838,282 | 6/1989 | Strasser et al. | 128/754 |
| 5,025,797 | 6/1991 | Baran | 128/754 |

FOREIGN PATENT DOCUMENTS 2625429 1/1988 France .

*Primary Examiner*—Max Hindenburg
*Assistant Examiner*—Guy V. Tucker
*Attorney, Agent, or Firm*—Benjamin J. Barish

[57] ABSTRACT

A hard tissue biopsy instrument includes an outer hollow needle attachable to a housing to project from one end thereof and having a sharpened outer tip; an inner hollow needle attachable to the housing within the outer hollow needle and having a milling outer tip, the inner hollow needle being rotatably and axially movable with respect to the outer hollow needle; and a rotary drive for rotating the inner hollow needle within the outer hollow needle.

16 Claims, 5 Drawing Sheets

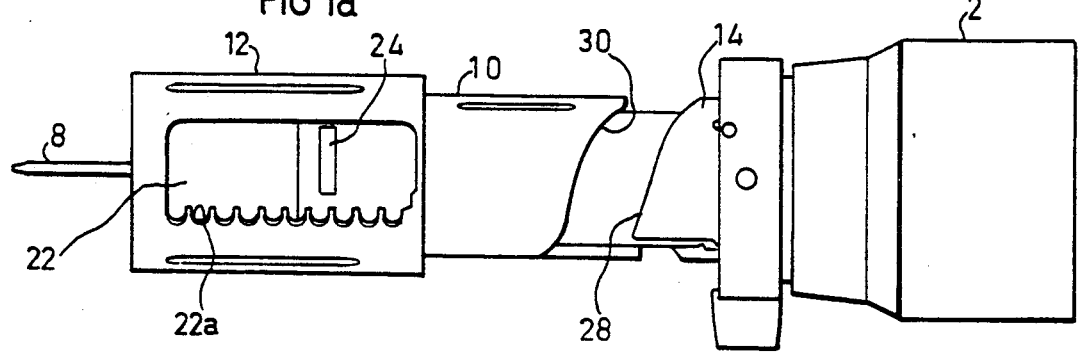
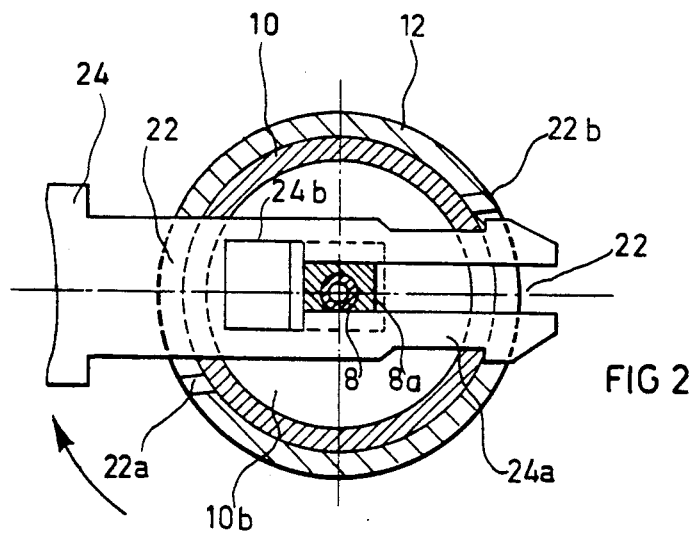
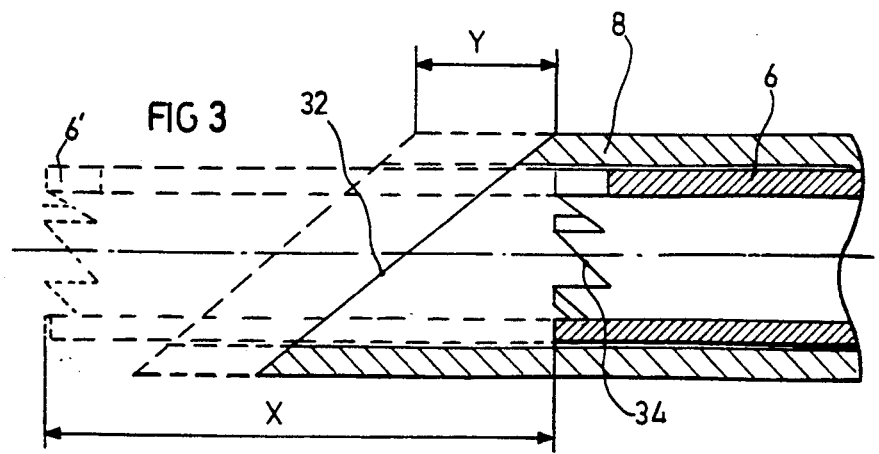

HARD TISSUE BIOPSY INSTRUMENT WITH ROTARY DRIVE

FIELD AND BACKGROUND OF THE INVENTION

The present invention relates to a hard tissue biopsy instrument particularly useful for removing hard tissue from the body of a subject. The invention is especially useful for removing a specimen of bone tissue and/or bone marrow, and is therefore described below with respect to such an application.

The conventional manner of drilling through, and/or of collecting specimens of, hard tissue, such as bone or skull tissue, is to use a conventional drill bit and to collect the particles by suction. For extracting bone marrow, a hollow needle is generally used. Thus, if it is desired to remove both bone tissue and bone marrow, two operations are generally required. Sometimes, it is also desired to remove cells of the bone marrow. This is usually done by a syringe, therefore requiring three operations in the conventional procedure.

OBJECTS AND BRIEF SUMMARY OF THE INVENTION

An object of the present invention is to provide an instrument having advantages in the above respects, and particularly an instrument which may be used for removing bone tissue, bone marrow, and/or marrow cells in a single operation.

According to the present invention, there is provided an instrument particularly useful for removing a specimen of a body tissue from a subject, comprising: a housing; an outer hollow needle carried by the housing to project from one end thereof, and an inner hollow needle carried by the housing within the outer hollow needle. The outer hollow needle has a sharpened outer, cutting tip; and the inner hollow needle has a milling outer tip. The inner hollow needle is rotatably and axially movable with respect to the outer hollow needle. The instrument also includes a rotary drive for rotating the inner hollow needle within the outer hollow needle.

According to additional features in the preferred embodiment of the invention described below, the instrument further includes presettable limit means for limiting the relative axial movement of the inner hollow needle with respect to the outer hollow needle. For the latter means in the described preferred embodiment; the housing includes an inner tubular section, and the presettable limit includes a sleeve manually rotatable on the inner tubular section to preset the relative axial movement of the inner hollow needle with respect to the outer hollow needle. The outer hollow needle is attachable to a second sleeve mounted for non-rotatable axial movement with respect to the inner tubular section of the housing.

According to still additional features in the described preferred embodiment, the instrument further includes presettable penetration means at the end of the housing and engageable with the subject's skin for presetting the penetration of the outer hollow needle through the subject's skin. The presettable penetration means, in the described instrument, comprises a cap presettable axially of the second sleeve. The cap further includes a clamping member manually movable from a clamping position with respect to the outer hollow needle to clamp the needle to the second sleeve, or to a releasing position with respect to the outer hollow needle to release the needle from the second sleeve.

An instrument constructed in accordance with the foregoing features is useful in many applications, but is particularly useful in removing bone tissue and bone marrow from a subject's body in one simple and efficient operation. In addition, when such an instrument is used for removing bone tissue and bone marrow, it also facilitates the removal of cells from the bone marrow by the use of a conventional syringe, as will be described more particularly below.

Further features and advantages of the invention will be apparent from the description below.

BRIEF DESCRIPTION OF THE DRAWINGS

The invention is herein described, by way of example only, with reference to the accompanying drawings, wherein:

FIG. 1a is a side elevational view illustrating the instrument of FIG. 1 in assembled condition;

FIG. 2 is a sectional view along line II—II of FIG. 1;

FIG. 3 is an enlarged fragmentary view illustrating the outer tips of the two hollow needles used in the instrument of FIG. 1, and particularly their different positions during use of the instrument.

DESCRIPTION OF A PREFERRED EMBODIMENT

CONSTRUCTION

Figure 1:
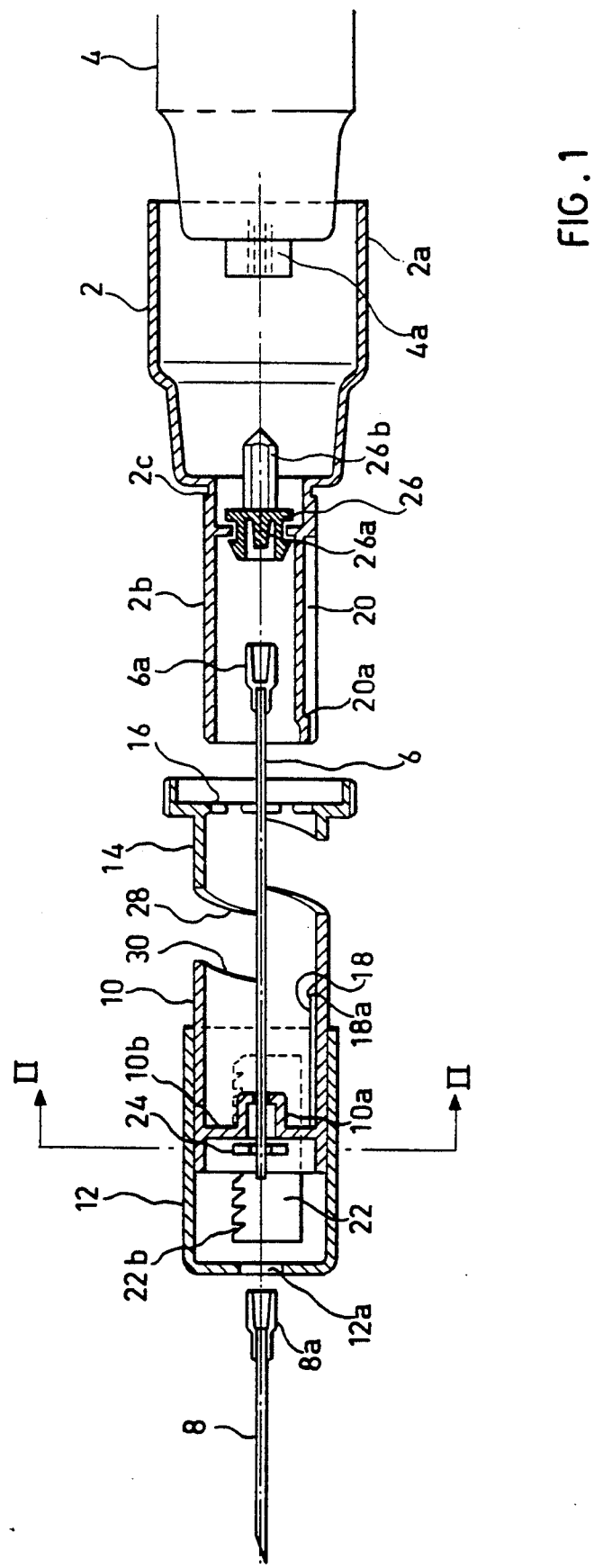
FIG. 1 is an exploded view illustrating one form of instrument constructed in accordance with the present invention.

With reference first to the exploded view of the instrument illustrated in the drawings, it will be seen that it comprises a housing, generally designated 2, adapted to be coupled at one end to an electric rotary motor 4. The opposite end of housing 2 detachably carries an inner hollow needle 6 to be coupled to the electric motor 4, and an outer hollow needle 8 to enclose the inner hollow needle 6. The outer hollow needle 8 is detachably coupled to a sleeve 10 slidably receivable at one end of housing 2, and slidably receiving at its opposite end a cap 12.

More particularly, housing 2 is formed with an enlarged section 2a to enclose the coupling portion to motor 4, and with a tubular section 2b for receiving sleeve 10 to which the outer hollow needle 8 is attached. Tubular section 2b of housing 2 further supports another sleeve 14 which serves as presettable limit for limiting the relative axial movement of the inner hollow needle 6 with respect to the outer hollow needle 8. Thus, one end of sleeve 14 is formed with an inner annular rib 16 receivable in an annular groove 2c at the juncture between the two housing sections 2a, 2b. Rib 16 permits sleeve 14 to be rotated with respect to the tubular section 2b of the housing, but does not permit it to be moved axially of that section.

Annular rib 16 may be continuous, but preferably it is interrupted around its circumference to facilitate the application of sleeve 14 to housing 2 by a snap-fit.

Sleeve 10, carrying the outer hollow needle 8, is mounted on tubular section 2b of the housing 2 in a manner permitting it to be movable axially of the housing, but not rotationally. For this purpose, sleeve 10 is formed on its inner face with an axially-extending rib or spline 18 received within an axially-extending groove 20 formed on the outer surface of housing tubular section 2b, thereby splining sleeve 10 to tubular section 2b. The axial groove 20 in tubular section 2b terminates short of the outer end of the tubular section, as shown at 20a; and the outer end of the axial rib 18 of sleeve 10 is formed with a curved enlargement 18a. This permits the sleeve 10 to be applied with a snap-fit to the tubular section 2b.

Cap 12 is formed with a central opening 12a through its end wall to permit the passage therethrough of the outer hollow needle 8, as well as of the inner hollow needle 6 enclosed within needle 8. Cap 12 is movable axially of sleeve 10 and may be preset at a preselected axial position on sleeve 10 in order to preset the penetration of the two needles through the subject's skin. For this purpose, cap 12 is formed with a transversely-extending slot 22 receiving a clamping member 24 extending completely through the slot, as shown particularly in FIG. 2. The width of slot 22 is slightly greater than the width of clamping member 24, permitting cap 12 to be slightly rotated with respect to the clamping member. In addition, the opposite edges of the clamping member are formed with a plurality of notches, as shown at 22a and 22b (FIG. 2).

Cap 12 may be preset to any axial position with respect to sleeve 10. This is done by first rotating the cap to unseat its notches 22a, 22b from clamping member 24, then moving the cap axially of sleeve 10 to the preselected position, and finally rotating the cap back to seat clamping member 24 in the notches 22a, 22b at the selected axial position of the cap with respect to the sleeve.

Clamping member 24 is also used for clamping or releasing the outer hollow needle 8 from sleeve 10. For this purpose, the outer hollow needle 8 includes a square enlargement or head 8a at one end. Clamping member 24 is formed with a split shank 24a, which split is enlarged at 24b. Split 24a defines a socket of the same dimensions as the square head 8a of the outer hollow needle 8, so that when the clamping member is in the position illustrated in FIG. 2, receiving needle head 8a within its split shank 24a, it clamps the outer hollow needle 8 to sleeve 10. In order to release the outer hollow needle from the sleeve, clamping member 24 is pressed further inwardly to receive the square head 8a of the outer hollow needle 8 in the enlarged socket 24b, thereby releasing the outer hollow needle and permitting its detachment from both cap 12 and sleeve 10.

The end of the outer hollow needle 8 formed with the square head 8a is also non-rotatably received within a square socket 10a centrally of an end wall 10b of sleeve 10 so that needle 8 is rotated by the rotation of sleeve 10.

The inner hollow needle 6 is coupled to motor 4 by a coupling member 26 rotatably mounted within tubular section 2b of the housing 2. For this purpose one end of coupling member 26 is formed with a square socket 26a receiving a square head 6a at the respective end of the inner hollow needle 6. The opposite end of coupling member 26 is formed with a hexagonal plug 26b adapted to be coupled to motor 4 via a hexagonal socket 4a in the motor drive shaft.

As briefly described above, sleeve 14 is mounted for rotary, non-axial movement with respect to tubular section 2b of the housing (via annular rib 16 of the sleeve received within annular groove 2c of the housing), whereas sleeve 10 is mounted for non-rotary, axial movement with respect to the housing tubular section 2b (via spline 18 receivable in groove 20). As also briefly described above, the inner hollow needle 6 is mounted for both rotary and axial movement with respect to the outer hollow needle 8. Sleeve 14 serves as a presettable limit for limiting the relative axial movement of the inner hollow needle 6 with respect to the outer hollow needle 8. For this purpose, sleeves 14 and 10 are both formed with abuttable ends of helical configuration, as shown at 28 and 30 respectively, such that the manual rotation of sleeve 14 changes the gap between the abuttable ends 28, 30.

FIG. 3 illustrates the outer tips of the inner hollow needle 6 and of the outer hollow needle 8. Thus, the outer hollow needle 8 is formed with a sharpened outer tip, as shown at 32, whereas the inner hollow needle 6 is formed with a milling outer tip, as shown at 34.

FIG. 3 further illustrates the relative positions of the two needles. Thus, the inner hollow needle 6 may be moved from its retracted position shown in full lines in FIG. 3, to its extended position as shown in broken lines at 6' in FIG. 3. The distance between the two axial positions of needle 6 with respect to needle 8 is indicated as "x", and is determined by the preset position of sleeve 14 with respect to sleeve 10. FIG. 3 also illustrates another displacement of needle 6 with respect to needle 8. This displacement, generally designated "y", is preselected by the position of cap 12 with respect to sleeve 10, as will be described more particularly below.

OPERATION

The manner of using the instrument illustrated in the drawings, for removing specimens of both bone tissue and bone marrow, in a single surgical procedure, will now be described particularly with reference to FIGS. 4a–4e.

Figure 4A:
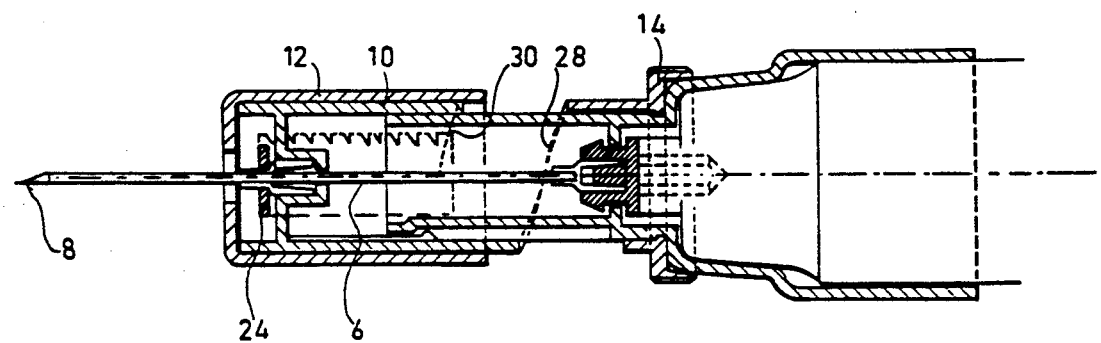
FIGS. 4a–4e illustrate different conditions of the instrument during its use for removing both bone tissue and blood marrow in a single operation.

FIG. 4a illustrates the condition of the instrument at the beginning of the surgical procedure, wherein it will be seen that cap 12 is moved to its retracted position with respect to sleeve 10, i.e., against the end of the sleeve; and sleeve 14 is rotated to have no gap between the helical ends 28, 30 of sleeves 14 and 10, respectively. Clamping member 24 is of course in its clamping position with its split shank 24a (FIG. 2) receiving the needle enlargement 8a of the outer hollow needle 8, to securely clamp the needle to sleeve 10. In this condition of the instrument, the inner hollow needle 6 is in its retracted position with respect to the outer hollow needle 8, as shown in full lines in FIG. 3.

The instrument is then grasped and pressed into the body tissue at the selected location until the outer hollow needle 8 engages the hard tissue (e.g., bone). This will be readily felt by the increased resistance to penetration when the outer needle 8 engages the bone.

Figure 4B:
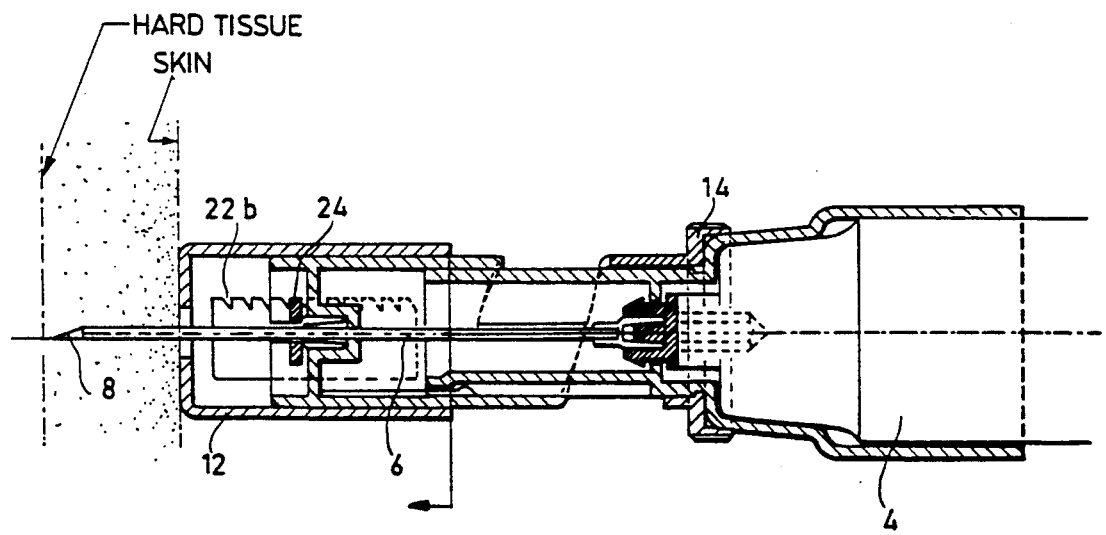

The outer cap 12 is then moved axially to engage the skin, as shown in FIG. 4b. As described earlier, this axial movement of the cap is easily effected by first rotating the cap to unseat its notches 22a, 22b from clamping member 24, then moving it axially to the selected position, and finally rotating it back to move the notches back into engagement with the clamping member.

Figure 4C:
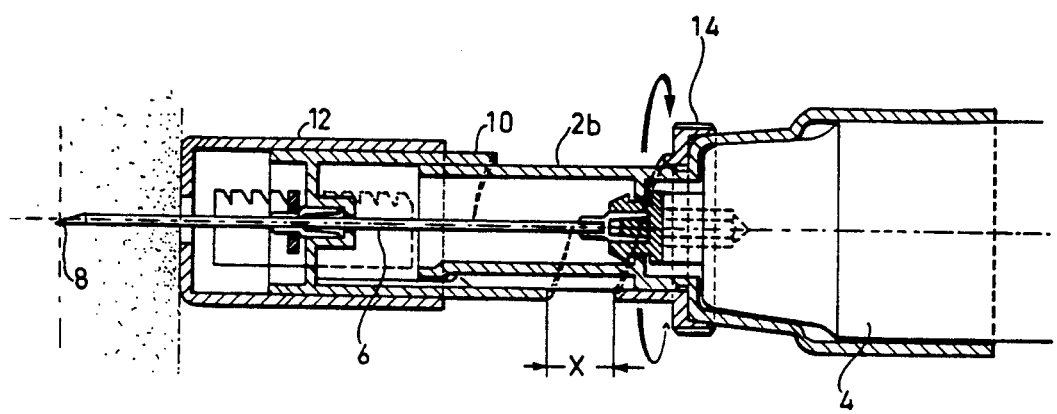

Sleeve 14 is then manually rotated to preset the distance "x" as shown in FIG. 4c. This is the distance determining how far the inner hollow needle 6 will project past the outer hollow needle 8 during the milling operation, i.e., the depth of penetration of the inner needle through the bone.

Figure 4D:
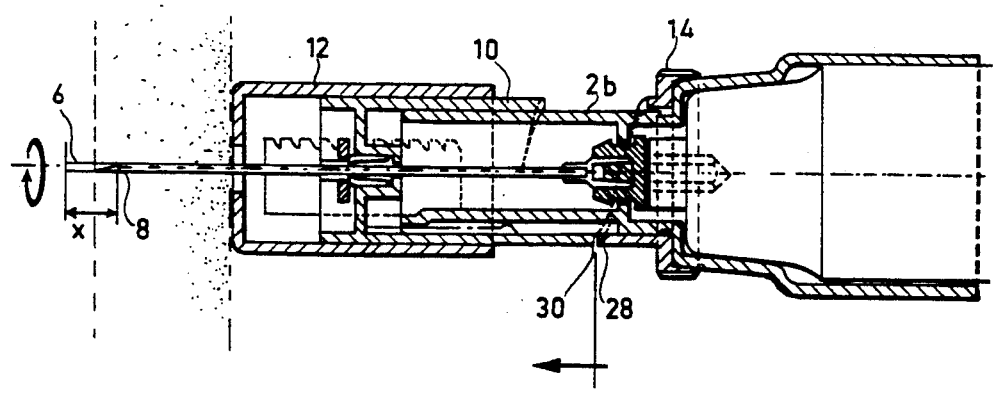

The electric motor 4 is then energized and the instrument is pressed inwardly. The inner hollow needle 6 is thus rotated so that its milling outer tip 34 mills an annular cut through the bone tissue until the helical end 28 of sleeve 14 engages the helical end 30 of sleeve 10. When this occurs, the inner hollow needle 6 will have moved the distance "x" shown in FIG. 3 and will receive a core of the cut bone, as well as of bone marrow adhering to the bone. This is the condition of the instrument as illustrated in FIG. 4d, wherein it will be seen that the inner hollow needle 6 has penetrated past the outer hollow needle 8 by the distance "x".

The sleeve 14 is then rotated in the opposite direction thus sliding back the housing tubular section 2b with respect to sleeve 10 and cap 12, since the end of cap 12 bears against the subject's skin and therefore does not move axially. The rotation of sleeve 14 thus moves the inner hollow needle 6 (carried by housing tubular section 2b) back to its retracted position with respect to the outer hollow needle 8, as shown in FIG. 4e.

Figure 4E:
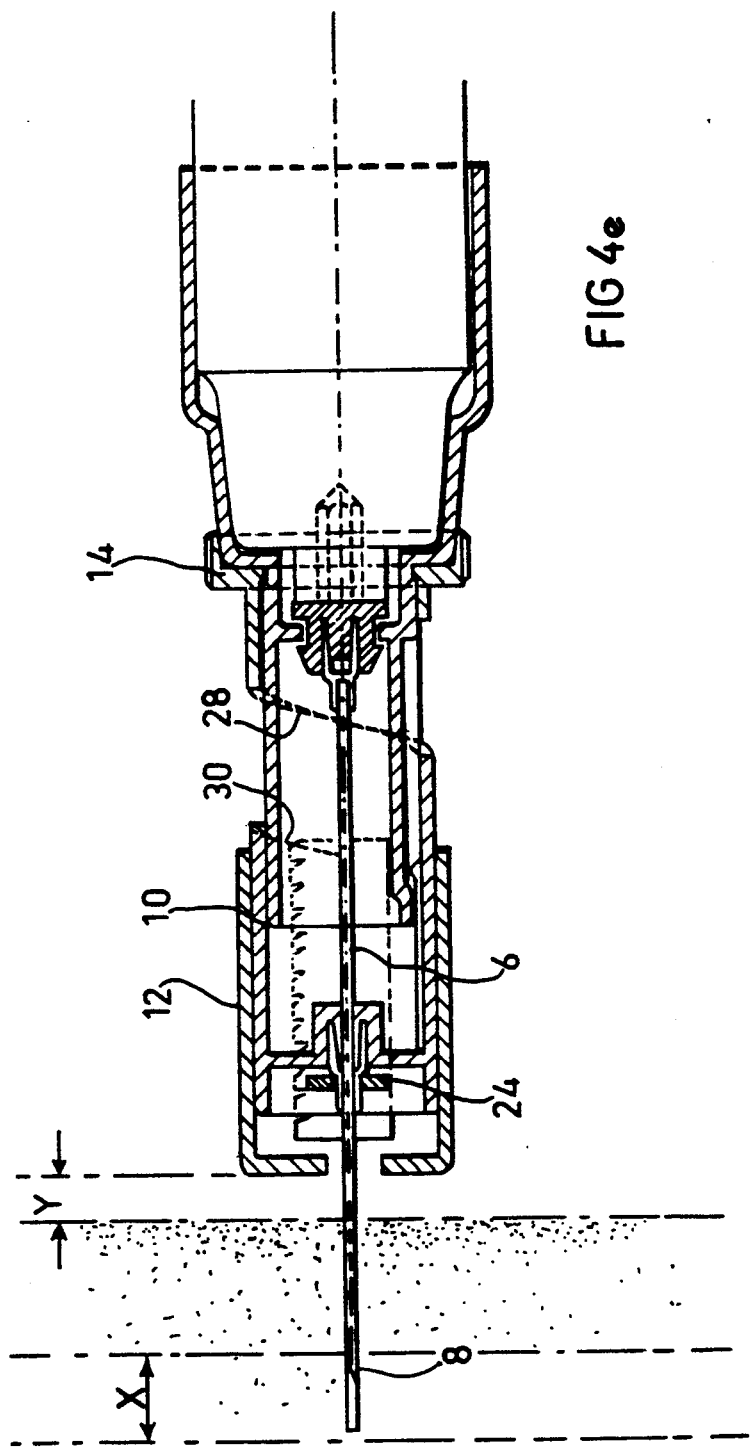

Next, cap 12 is moved inwardly of sleeve 10, in the manner described above, so as to space the end of the cap from the skin the distance "y" shown in FIG. 4e. The instrument is then firmly pressed inwardly, which causes the outer hollow needle 8 to become firmly wedged or anchored in the previously-cut opening in the bone.

Finally, clamping member 24 is moved to its releasing position with respect to the outer hollow needle 8, i.e., with the enlarged socket 24b of the clamping member straddling the square head 8a of the needle as shown in FIG. 2, permitting the instrument to be detached from the outer hollow needle 8 now firmly anchored in the bone.

After the instrument has thus been removed from the outer hollow needle 8, the inner hollow needle 6 may be removed, and then the core sample of blood tissue and bone marrow received within its interior may be removed using a stylet. The hollow outer needle 8, now firmly anchored in the bone, may then be used for drawing cells from the interior of the bone by the use of a conventional syringe. After this has been accomplished, the outer hollow needle may be removed by merely pulling it out from the bone.

While the invention has been described with respect to one preferred embodiment, it will be appreciated that many variations, modifications and other applications of the invention may be made.

What is claimed is:

1. A hard tissue biopsy instrument, comprising:
   a housing;
   an outer hollow needle carried by said housing to project from one end thereof;
   an inner hollow needle carried by said housing within said outer hollow needle, said inner hollow needle being rotatably and axially movable with respect to said outer hollow needle;
   the outer hollow needle having a sharpened outer cutting tip, and the inner hollow needle having an outer milling tip;
   a manually presettable limit for manually presetting the axial movement of the inner milling-tip needle with respect to the outer cutting-tip needle;
   and a drive for rotating said inner milling-tip needle within said outer cutting-tip needle and for moving said inner milling-tip needle outwardly of said outer cutting-tip needle according to said manually-preset limit.

2. The instrument according to claim 1 wherein said housing includes an inner tubular section, and said presettable limit includes a sleeve manually rotatable on said inner tubular section to preset the relative axial movement of the inner hollow needle with respect to the outer hollow needle 3. The instrument according to claim 2, wherein said outer hollow needle is attachable to a second sleeve mounted for non-rotatable axial movement with respect to said inner tubular section of the housing.

4. The instrument according to claim 3, wherein both of said sleeves are formed with abuttable ends of helical configuration such that manual rotation of the first-mentioned sleeve changes the gap between said abuttable ends of the two sleeves and thereby presets the relative axial movement of the inner hollow needle with respect to the outer hollow needle.

5. The instrument according to claim 3, further including a presettable penetration means at said one end of the housing and engageable with the subject's skin for presetting the penetration of the outer hollow needle through the subject's skin.

6. The instrument according to claim 5, wherein said presettable penetration means comprises a cap presettable along the longitudinal axis of said second sleeve.

7. The instrument according to claim 6, wherein said cap further includes a clamping member manually movable from a clamping position with respect to said outer hollow needle clamping same to said second sleeve, or to a releasing position with respect to said outer hollow needle for releasing same from said second sleeve.

8. The instrument according to claim 7, wherein said cap is formed with a plurality of notches spaced axially thereof, and wherein said clamping member is receivable in one of said notches for presetting the axial position of said cap with respect to said second sleeve.

9. The instrument according to claim 7, wherein said outer hollow needle includes an enlarged head, and said clamping member includes a socket engageable with said enlarged head in the clamping position of the clamping member.

10. The instrument according to claim 1, wherein said inner hollow needle is detachably coupled to one end of a coupling member rotatably supported within said housing, the other end of said rotatable coupling member being detachably coupled to said rotary drive.

11. The instrument according to Claim 10, wherein said rotatable coupling member is formed with a non-circular socket at one end receiving a complementary non-circular plug at the respective end of said inner hollow needle, the opposite end of said rotary coupling member being formed with a hexagonal plug received in a hexagonal socket of said rotary drive.

12. A hard tissue biopsy instrument, comprising:
    a housing;
    an outer hollow needle attachable to said housing to project from one end thereof and having a sharpened outer, cutting tip;
    an inner hollow needle attachable to said housing within said outer hollow needle, and having an outer milling tip, said inner hollow needle being rotatably and axially movable with respect to said outer hollow needle;
    a manually presettable limit for manually presetting the axial movement of the inner milling-tip needle with respect to the outer cutting-tip needle;
    presettable penetration means at said one end of the housing engageable with the subject's skin for presetting the penetration of the outer hollow needle through the subject's skin;

and a drive for rotating said inner milling-tip needle within said outer cutting-tip needle and for moving said inner milling-tip needle outwardly of said outer cutting-tip needle according to said manually-preset limit.

13. The instrument according to claim 12 wherein said housing includes an inner tubular section, and said presettable limit includes a sleeve manually rotatable on said inner tubular section to preset the relative axial movement of the inner hollow needle with respect to the outer hollow needle.

14. The instrument according to claim 13 wherein said outer hollow needle is attachable to a second sleeve mounted for non-rotatable axial movement with respect to said inner tubular section of the housing.

15. The instrument according to claim 14, wherein both of said sleeves are formed with abuttable ends of helical configuration such that manual rotation of the first-mentioned sleeve changes the gap between said abuttable ends of the two sleeves and thereby presets the relative axial movement of the inner hollow needle with respect to the outer hollow needle.

16. The instrument according to claim 12 wherein said presettable penetration means comprises a cap presettable along the longitudinal axis of said second sleeve.

* * * * *